United States Patent
Sigg et al.

(10) Patent No.: US 9,220,631 B2
(45) Date of Patent: Dec. 29, 2015

(54) SYRINGE

(71) Applicant: Novartis AG, Basel (CH)

(72) Inventors: Juergen Sigg, Loerrach (DE);
Christophe Royer, Munich (DE);
Andrew Mark Bryant, Basel Land
(CH); Heinrich Martin Buettgen,
Rheinfelden (CH); Marie Picci,
Ranspack-le-bas (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/750,352

(22) Filed: Jan. 25, 2013

(65) Prior Publication Data

US 2014/0012227 A1   Jan. 9, 2014

(30) Foreign Application Priority Data

| Jul. 30, 2012 | (EP) | ..................... 12174860 |
| Oct. 23, 2012 | (EP) | ..................... 12189649 |
| Nov. 16, 2012 | (AU) | ................. 2012101677 |
| Nov. 16, 2012 | (AU) | ................. 2012101678 |
| Nov. 16, 2012 | (DE) | ............ 20 2012 011 016 U |
| Nov. 23, 2012 | (DE) | ............ 20 2012 011 259 U |
| Nov. 23, 2012 | (DE) | ............ 20 2012 011 260 U |
| Dec. 3, 2012  | (EP) | ..................... 12195360 |
| Jan. 23, 2013 | (AU) | ................. 2013100070 |
| Jan. 23, 2013 | (AU) | ................. 2013100071 |
| Jan. 23, 2013 | (DE) | ............ 20 2013 000 688 U |

(51) Int. Cl.
*A61M 5/00*   (2006.01)
*A61F 9/00*   (2006.01)
*A61M 5/178*  (2006.01)
(Continued)

(52) U.S. Cl.
CPC ............. *A61F 9/0008* (2013.01); *A61K 9/0019* (2013.01); *A61K 9/0048* (2013.01); *A61K 38/179* (2013.01); *A61M 5/002* (2013.01); *A61M 5/178* (2013.01); *A61M 5/28* (2013.01); *A61M 5/31* (2013.01); *A61M 5/315* (2013.01); *A61M 5/31505* (2013.01); *A61M 5/31513* (2013.01);
(Continued)

(58) Field of Classification Search
CPC ........ A61K 9/0048; A61F 9/008; A61M 5/31
USPC .................................................. 604/218, 294
See application file for complete search history.

(56) References Cited

U.S. PATENT DOCUMENTS 6,090,081 A * 7/2000 Sudo et al. ..................... 604/230
7,141,042 B2 * 11/2006 Lubrecht ....................... 604/230
(Continued)

FOREIGN PATENT DOCUMENTS

AU   2012101677 A4   12/2012
AU   2012101678 A4   12/2012
(Continued)

OTHER PUBLICATIONS

Badkar et al., "Development of biotechnology products in pre-filled syringes: technical considerations and approaches", AAPS PharmSciTech, vol. 12, No. 2, pp. 564-572, (Jun. 2011).
(Continued)

*Primary Examiner* — Aarti B Berdichevsky
(74) *Attorney, Agent, or Firm* — Michael Mazza

(57) ABSTRACT

The present invention relates to a syringe, particularly to a small volume syringe such as a syringe suitable for ophthalmic injections.

26 Claims, 1 Drawing Sheet

Fig 2

(51) Int. Cl.
*A61M 5/315* (2006.01)
*A61K 9/00* (2006.01)
*A61K 38/17* (2006.01)
*A61M 5/28* (2006.01)
*A61M 5/31* (2006.01)

(52) U.S. Cl.
CPC ............... *A61M 2005/3104* (2013.01); *A61M 2005/3139* (2013.01)

(56) References Cited

U.S. PATENT DOCUMENTS

| | | | |
|---|---|---|---|
| 7,303,748 | B2* | 12/2007 | Wiegand et al. ............ 424/134.1 |
| 2006/0172944 | A1* | 8/2006 | Wiegand et al. ................ 514/12 |
| 2006/0293270 | A1 | 12/2006 | Adamis et al. |
| 2007/0190058 | A1* | 8/2007 | Shams ........................ 424/145.1 |
| 2008/0312607 | A1* | 12/2008 | Delmotte et al. ............. 604/230 |
| 2010/0310309 | A1 | 12/2010 | Abendroth et al. |
| 2011/0257601 | A1 | 10/2011 | Furfine et al. |
| 2011/0276005 | A1* | 11/2011 | Hioki et al. ................... 604/187 |
| 2012/0078224 | A1 | 3/2012 | Lerner et al. |
| 2013/0012918 | A1 | 1/2013 | Foster |
| 2014/0249484 | A1* | 9/2014 | Jones et al. ................... 604/230 |

FOREIGN PATENT DOCUMENTS

| | | |
|---|---|---|
| CN | 201578690 U | 9/2010 |
| DE | 10 2008 005938 A1 | 7/2009 |
| EP | 0264273 A2 | 4/1988 |
| EP | 0879611 A2 | 11/1998 |
| EP | 2371406 | 10/2011 |
| JP | 2001-104480 | 4/2001 |
| JP | 2002241264 A2 | 8/2002 |
| WO | 97/44068 A1 | 11/1997 |
| WO | 2006047325 A1 | 5/2006 |
| WO | 2006128564 A1 | 12/2006 |
| WO | WO 2007/035621 A1 | 3/2007 |
| WO | 2007084765 A2 | 7/2007 |
| WO | WO 2007/149334 A2 | 12/2007 |
| WO | WO2010/060748 | 6/2010 |
| WO | 2010136492 | 12/2010 |
| WO | WO 2011/123722 A1 | 10/2011 |
| WO | WO2011/135067 | 11/2011 |
| WO | WO 2012/134528 A1 | 10/2012 |
| WO | WO 2012/149040 A2 | 11/2012 |
| WO | 2014/005728 A1 | 1/2014 |

OTHER PUBLICATIONS

Ausubel et al., "Current Protocols in Molecular Biology", 7.7.18 of Current protocols in Molecular Biology, eds., supplement 30, (1987).
Badkar et al., Analysis of Two Commercially Available Bortezomib Products : Differences in Assay of Active Agent and Impurity Profile >> AAPS PharmaSciTech, vol. 12, No. 2, pp. 564-572, (Jun. 2011).
Schoenknecht, "Requirements on pre-fillable glass suringes", AAPS National Biotechnology Conference 2007—Abstract No. NBC07-000488, 2007.
Holash et al., "VEGF-Trap: A VEGF blocker with potent anitumor effects", PNAS USA, vol. 99, No. 17, pp. 11393-11398, (Aug. 20, 2002).
Riely & Miller, "Vascular Endothelial Growth Factor Trap in Non-Small Cell lung Cancer", Clin Cancer Res, 13:4623-7s, (Aug. 1, 2007).
Li et al., "KH906, a recombinant human VEGF receptor fusion protein, is a new effective topical treatment for corneal neovascularization", Molecular Vision, 17:797-803,(Mar. 25, 2011).
Smith & Waterman, "Comparison of Biosequences", Adv Appl. Math, 2:482-489, (1981).
Chan et al: "Syringe Siliconization Process Investigation and Optimization" Journal of Pharmaceutical Science and Technology, Issue 66, pp. 137, 147-148, Mar. 2012.
Lankers: "The Relationship Between Silicone Layer Thickness, Free Silicone Oil and Protein Aggregation in Prefilled Syringes" 2010 AAPS National Biotechnology Conference San Francisco, Slides 25, 39, 46, May 19, 2010.
Majumdar et al: "Evaluation of the Effect of Syringe Surfaces on Protein Formulations" Journal of Pharmaceutical Sciences, Issue 100, pp. 2563-2573, Jul. 2011.
Bakri and Ekdawi: "Intravitreal Silicone Oil Droplets after Intravitreal Drug Injections" Retina, Issue 28, pp. 996-1001, Jul. 2008.
Daikyo Ru Crystal Zenith Insert Needle Syringe System, West Delivering Innovative Solutions, 2010.
Meyer et al: "Steps for a Safe Intravitreal Injection Technique",Meyer et al. "Steps for a Safe Intravitreal Injection Technique"Retinal Physician, p. 3, Jul. 1, 2009.
"Biopharmaceuticals—SPE applications", RapID Particle Systems, Single Particle Explore, D6a, Sep. 28, 2015, http //www.particle-explorer.com/yourapplications/biopharaceuticals/index.html[Sep. 16, 2015 11:12:45].
Email dated Sep. 9, 2015 from Elizabeth Scuderl, Senior meeting Manager, AAPS to Teresa Homnch re Inquiry about publication of conference abstract.
Tibor Hlobik: "Reducing quality risks to drug products and meeting needs of patients with enhanced components for prefilled syringe systems". West Delivering Innovative Solutions, www.ondrugdelivery.com, 2012 No. 33, pp. 32-34.
Summary of Product Characteristics—Zaltrap (undated).
"Ranibizumab", Scientific Discussion, EMEA, 2007, pp. 1-54.
"Avastin", Scientific Discussion, EMEA, 2005, pp. 1-61.
Melmet Selim Kocabora, et al. "Intreavitreal silicone oil droplets following pegaptanib injection", Acta Ophthalmologica, 2010 e44-345.
N. Clunas, et al: "Ranibizumab pre-filled syringe: recently approved innovation in the Eurpean Union with the potential to reduce infection risk, improve does accuracy, and enhance efficient treatment administration". Congress on Controversies in Ophthamology, Abstract, 2014.
"COPHy Poster List—Group A"(Poster 17), The 5th World congress on Controversies in Opthalmology (COPHy) Mar. 20-23, 2014, Lisbon, Portugal.

* cited by examiner

SYRINGE

TECHNICAL FIELD

The present invention relates to a syringe, particularly to a small volume syringe such as a syringe suitable for ophthalmic injections.

BACKGROUND ART

Many medicaments are delivered to a patient in a syringe from which the user can dispense the medicament. If medicament is delivered to a patient in a syringe it is often to enable the patient, or a caregiver, to inject the medicament. It is important for patient safety and medicament integrity that the syringe and the contents of that syringe are sufficiently sterile to avoid infection, or other, risks for patients. Sterilisation can be achieved by terminal sterilisation in which the assembled product, typically already in its associated packaging, is sterilised using heat or a sterilising gas.

For small volume syringes, for example those for injections into the eye in which it is intended that about 0.1 ml or less of liquid is to be injected the sterilisation can pose difficulties that are not necessarily associated with larger syringes. Changes in pressure, internal or external to the syringe, can cause parts of the syringe to move unpredictably, which may alter sealing characteristics and potentially compromise sterility. Incorrect handling of the syringe can also pose risks to product sterility.

Furthermore, certain therapeutics such as biologic molecules are particularly sensitive to sterilisation, be it cold gas sterilisation, thermal sterilisation, or irradiation. Thus, a careful balancing act is required to ensure that while a suitable level of sterilisation is carried out, the syringe remains suitably sealed, such that the therapeutic is not compromised. Of course, the syringe must also remain easy to use, in that the force required to depress the plunger to administer the medicament must not be too high.

There is therefore a need for a new syringe construct which provides a robust seal for its content, but which maintains ease of use.

DISCLOSURE OF THE INVENTION

The present invention provides a pre-filled syringe, the syringe comprising a body, a stopper and a plunger, the body comprising an outlet at an outlet end and the stopper being arranged within the body such that a front surface of the stopper and the body define a variable volume chamber from which a fluid can be expelled though the outlet, the plunger comprising a plunger contact surface at a first end and a rod extending between the plunger contact surface and a rear portion, the plunger contact surface arranged to contact the stopper, such that the plunger can be used to force the stopper towards the outlet end of the body, reducing the volume of the variable volume chamber, characterised in that the fluid comprises an ophthalmic solution. In one embodiment, the ophthalmic solution comprises a VEGF-antagonist.

In one embodiment, the syringe is suitable for ophthalmic injections, more particularly intravitreal injections, and as such has a suitably small volume. The syringe may also be silicone oil free, or substantially silicone oil free, or may comprise a low level of silicone oil as lubricant. In one embodiment, despite the low silicone oil level, the stopper break loose and slide force is less than 20N.

For ophthalmic injections, it is particularly important for the ophthalmic solution to have particularly low particle content. In one embodiment, the syringe meets US Pharmacopeia standard 789 (USP789).

Syringe

The body of the syringe may be a substantially cylindrical shell, or may include a substantially cylindrical bore with a non circular outer shape. The outlet end of the body includes an outlet through which a fluid housed within the variable volume chamber can be expelled as the volume of said chamber is reduced. The outlet may comprise a projection from the outlet end through which extends a channel having a smaller diameter than that of the variable volume chamber. The outlet may be adapted, for example via a luer lock type connection, for connection to a needle or other accessory such as a sealing device which is able to seal the variable volume chamber, but can be operated, or removed, to unseal the variable volume chamber and allow connection of the syringe to another accessory, such as a needle. Such a connection may be made directly between the syringe and accessory, or via the sealing device. The body extends along a first axis from the outlet end to a rear end.

The body may be made from a plastic material (e.g. a cyclic olefin polymer) or from glass and may include indicia on a surface thereof to act as an injection guide. In one embodiment the body may comprise a priming mark. This allows the physician to align a pre-determined part of the stopper (such as the tip of the front surface or one of the circumferential ribs, discussed later) or plunger with the mark, thus expelling excess ophthalmic solution and any air bubbles from the syringe. The priming process ensures that an exact, pre-determined dosage is administered to the patient.

The stopper may be made from rubber, silicone or other suitable resiliently deformable material. The stopper may be substantially cylindrical and the stopper may include one or more circumferential ribs around an outer surface of the stopper, the stopper and ribs being dimensioned such that the ribs form a substantially fluid tight seal with an internal surface of the syringe body. The front surface of the stopper may be any suitable shape, for example substantially planar, substantially conical or of a domed shape. The rear surface of the stopper may include a substantially central recess. Such a central recess could be used to connect a plunger to the stopper using a snap fit feature or thread connection in a known manner. The stopper may be substantially rotationally symmetric about an axis through the stopper.

The plunger comprises a plunger contact surface and extending from that a rod extends from the plunger contact surface to a rear portion. The rear portion may include a user contact portion adapted to be contacted by a user during an injection event. The user contact portion may comprise a substantially disc shaped portion, the radius of the disc extending substantially perpendicular to the axis along which the rod extends. The user contact portion could be any suitable shape. The axis along which the rod extends may be the first axis, or may be substantially parallel with the first axis.

The syringe may include a backstop arranged at a rear portion of the body. The backstop may be removable from the syringe. If the syringe body includes terminal flanges at the end opposite the outlet end the backstop may be configured to substantially sandwich terminal flanges of the body as this prevent movement of the backstop in a direction parallel to the first axis.

The rod may comprise at least one rod shoulder directed away from the outlet end and the backstop may include a backstop shoulder directed towards the outlet end to cooperate with the rod shoulder to substantially prevent movement of the rod away from the outlet end when the backstop shoulder and rod shoulder are in contact. Restriction of the movement of the rod away from the outlet end can help to maintain sterility during terminal sterilisation operations, or other operations in which the pressure within the variable volume chamber or outside the chamber may change. During such operations any gas trapped within the variable volume chamber, or bubbles that may form in a liquid therein, may change in volume and thereby cause the stopper to move. Movement of the stopper away from the outlet could result in the breaching of a sterility zone created by the stopper. This is particularly important for low volume syringes where there are much lower tolerances in the component sizes and less flexibility in the stopper. The term sterility zone as used herein is used to refer to the area within the syringe that is sealed by the stopper from access from either end of the syringe. This may be the area between a seal of the stopper, for example a circumferential rib, closest to the outlet and a seal of the stopper, for example a circumferential rib, furthest from the outlet. The distance between these two seals defines the sterility zone of the stopper since the stopper is installed into the syringe barrel in a sterile environment.

To further assist in maintaining sterility during the operations noted above the stopper may comprise at a front circumferential rib and a rear circumferential rib and those ribs may be separated in a direction along the first axis by at least 3 mm, by at least 3.5 mm, by at least 3.75 mm or by 4 mm or more. One or more additional ribs (for example 2, 3, 4 or 5 additional ribs, or between 1-10, 2-8, 3-6 or 4-5 additional ribs) may be arranged between the front and rear ribs. In one embodiment there are a total of three circumferential ribs.

A stopper with such an enhanced sterility zone can also provide protection for the injectable medicament during a terminal sterilisation process. More ribs on the stopper, or a greater distance between the front and rear ribs can reduce the potential exposure of the medicament to the sterilising agent. However, increasing the number of ribs can increase the friction between the stopper and syringe body, reducing ease of use. While this may be overcome by increasing the siliconisation of the syringe, such an increase in silicone oil levels is particularly undesirable for syringes for ophthalmic use.

The rod shoulder may be arranged within the external diameter of the rod, or may be arranged outside the external diameter of the rod. By providing a shoulder that extends beyond the external diameter of the rod, but still fits within the body, the shoulder can help to stabilise the movement of the rod within the body by reducing movement of the rod perpendicular to the first axis. The rod shoulder may comprise any suitable shoulder forming elements on the rod, but in one embodiment the rod shoulder comprises a substantially disc shaped portion on the rod.

In one embodiment of the syringe, when arranged with the plunger contact surface in contact with the stopper and the variable volume chamber is at its intended maximum volume there is a clearance of no more than about 2 mm between the rod shoulder and backstop shoulder. In some embodiments there is a clearance of less than about 1.5 mm and in some less than about 1 mm. This distance is selected to substantially limit or prevent excessive rearward (away from the outlet end) movement of the stopper.

In one embodiment the variable volume chamber has an internal diameter greater than 5 mm or 6 mm, or less than 3 mm or 4 mm. The internal diameter may be between 3 mm and 6 mm, or between 4 mm and 5 mm.

In another embodiment the syringe is dimensioned so as to have a nominal maximum fill volume of between about 0.1 ml and about 1.5 ml. In certain embodiments the nominal maximum fill volume is between about 0.5 ml and about 1 ml. In certain embodiments the nominal maximum fill volume is about 0.5 ml or about 1 ml, or about 1.5 ml.

The length of the body of the syringe may be less than 70 mm, less than 60 mm or less than 50 mm. In one embodiment the length of the syringe body is between 45 mm and 50 mm.

In one embodiment, the syringe is filled with between about 0.01 ml and about 1.5 ml (for example between about 0.05 ml and about 1 ml, between about 0.1 ml and about 0.5 ml, between about 0.15 ml and about 0.175 ml) of a VEGF antagonist solution. In one embodiment, the syringe is filled with 0.165 ml of a VEGF antagonist solution. Of course, typically a syringe is filled with more than the desired dose to be administered to the patient, to take into account wastage due to "dead space" within the syringe and needle. There may also be a certain amount of wastage when the syringe is primed by the physician, so that it is ready to inject the patient.

Thus, in one embodiment, the syringe is filled with a dosage volume (i.e. the volume of medicament intended for delivery to the patent) of between about 0.01 ml and about 1.5 ml (e.g. between about 0.05 ml and about 1 ml, between about 0.1 ml and about 0.5 ml) of a VEGF antagonist solution. In one embodiment, the dosage volume is between about 0.03 ml and about 0.05 ml. For example, for Lucentis, the dosage volume is 0.05 ml or 0.03 ml (0.5 mg or 0.3 mg) of a 10 mg/ml injectable medicament solution; for Eylea, the dosage volume is 0.05 ml of a 40 mg/ml injectable medicament solution. Although unapproved for ophthalmic indications, bevacizumab is used off-label in such ophthalmic indications at a concentration of 25 mg/ml; typically at a dosage volume of 0.05 ml (1.25 mg). In one embodiment, the extractable volume from the syringe (that is the amount of product obtainable from the syringe following filling, taking into account loss due to dead space in the syringe and needle) is about 0.09 ml.

In one embodiment the length of the syringe body is between about 45 mm and about 50 mm, the internal diameter is between about 4 mm and about 5 mm, the fill volume is between about 0.12 and about 0.3 ml and the dosage volume is between about 0.03 ml and about 0.05 ml.

As the syringe contains a medicament solution, the outlet may be reversibly sealed to maintain sterility of the medicament. This sealing may be achieved through the use of a sealing device as is known in the art. For example the OVS™ system which is available from Vetter Pharma International GmbH.

It is typical to siliconise the syringe in order to allow ease of use, i.e. to apply silicone oil to the inside of the barrel, which decreases the force required to move the stopper. However, for ophthalmic use, it is desirable to decrease the likelihood of silicone oil droplets being injected into the eye. With multiple injections, the amount of silicone droplets can build up in the eye, causing potential adverse effects, including "floaters" and an increase in intra-ocular pressure. Furthermore, silicone oil can cause proteins to aggregate. A typical 1 ml syringe comprises 100-800 µg silicone oil in the barrel, though a survey of manufacturers reported that 500-1000 µg was typically used in pre-filled syringes (Badkar et al. 2011, AAPS PharmaSciTech, 12(2):564-572). Thus, in one embodiment, a syringe according to the invention comprises less than about 800 µg (i.e. about less than about 500 µg, less than about 300 µg, less than about 200 µg, less than about 100 µg, less than about 75 µg, less than about 50 µg, less than about 25 µg, less than about 15 µg, less than about 10 µg) silicone oil in the barrel. If the syringe comprises a low level of silicone oil, this may be more than about 1 µg, more than about 3 μg, more than about 5 μg, more than about 7 μg or more than about 10 μg silicone oil in the barrel. Thus, in one embodiment, the syringe may comprise about 1 μg-about 500 μg, about 3 μg-about 200 μg, about 5 μg-about 10 μg or about 10 μg-about 50 μg silicone oil in the barrel. Methods for measuring the amount of silicone oil in such a syringe barrel are known in the art and include, for example, differential weighing methods and quantitation by infrared-spectroscopy of the oil diluted in a suitable solvent. Various types of silicone oil are available, but typically either DC360 (Dow Corning®; with a viscosity of 1000 cP) or DC365 emulsion (Dow Corning®; DC360 oil with a viscosity of 350 cP) are used for syringe siliconisation. In one embodiment, the pre-filled syringe of the invention comprises DC365 emulsion.

During testing it was surprisingly found that, for syringes having small dimensions, such as those discussed above, and particularly those described in conjunction with the Figures below, the break loose and sliding forces for the stopper within the syringe are substantially unaffected by reducing the siliconisation levels far below the current standard to the levels discussed here. This is in contrast to conventional thinking that would suggest that if you decrease the silicone oil level, the forces required would increase (see e.g. Schoenknecht. AAPS National Biotechnology Conference 2007—Abstract no. NBC07-000488, which indicates that while 400 μg silicone oil is acceptable, usability improves when increased to 800 μg). Having too great a force required to move the stopper can cause problems during use for some users, for example accurate dose setting or smooth dose delivery may be made more difficult if significant strength is required to move, and/or keep in motion, the stopper. Smooth administration is particularly important in sensitive tissues such as the eye, where movement of the syringe during administration could cause local tissue damage. Break loose and slide forces for pre-filled syringes known in the art are typically in the region of less than 20N, but where the pre-filled syringes contain about 100 μg-about 800 μg silicone oil. In one embodiment the glide/slide force for the stopper within the pro-filled syringe is less than about 11N or less than 9N, less than 7N, less than 5N or between about 3N to 5N. In one embodiment, the break loose force is less than about 11N or less than 9N, less than 7N, less than 5N or between about 2N to 5N. Note that such measurements are for a filled syringe, rather than an empty syringe. The forces are typically measured at a stopper travelling speed of 190 mm/min. In one embodiment, the forces are measured with a 30 G×0.5 inch needle attached to the syringe. In one embodiment, the syringe has a nominal maximal fill volume of between about 0.5 ml and 1 ml, contains less than about 100 μg silicone oil and has a break loose force between about 2N to 5N.

In one embodiment the syringe barrel has an internal coating of silicone oil that has an average thickness of about 450 nm or less (i.e. 400 nm or less, 350 nm or less, 300 nm or less, 200 nm or less, 10 nm or less, 50 nm or less, 20 nm or less). Methods to measure the thickness of silicone oil in a syringe are known in the art and include the rap.ID Layer Explorer® Application, which can also be used to measure the mass of silicone oil inside a syringe barrel.

In one embodiment, the syringe is silicone oil free, or substantially silicone oil free. Such low silicone oil levels can be achieved by using uncoated syringe barrels and/or by avoiding the use of silicone oil as a lubricant for product contacting machine parts, or pumps in the syringe assembly and fill line. A further way to reduce silicone oil and inorganic silica levels in a pre-filled syringe is to avoid the use of silicone tubing in filling lines, for example between storage tanks and pumps.

The syringe according to the invention may also meet certain requirements for particulate content. In one embodiment, the ophthalmic solution comprises no more than 2 particles ≥50 μm in diameter per ml. In one embodiment, the ophthalmic solution comprises no more than 5 particles ≥25 μm in diameter per ml. In one embodiment, the ophthalmic solution comprises no more than 50 particles ≥10 μm in diameter per ml. In one embodiment, the ophthalmic solution comprises no more than 2 particles ≥50 μm in diameter per ml, no more than 5 particles ≥25 μm in diameter per ml and no more than 50 particles ≥10 μm in diameter per ml. In one embodiment, a syringe according to the invention meets USP789 (United States Pharmacopoeia: Particulate Matter in Ophthalmic Solutions). In one embodiment the syringe has low levels of silicone oil sufficient for the syringe to meet USP789.

VEGF Antagonists
Antibody VEGF Antagonists

VEGF is a well-characterised signal protein which stimulates angiogenesis. Two antibody VEGF antagonists have been approved for human use, namely ranibizumab (Lucentis®) and bevacizumab (Avastin®).

Non-Antibody VEGF Antagonist

In one aspect of the invention, the non-antibody VEGF antagonist is an immunoadhesin. One such immuoadhesin is aflibercept (Eylea®), which has recently been approved for human use and is also known as VEGF-trap (Holash et al. (2002) *PNAS USA* 99:11393-98; Riely & Miller (2007) *Clin Cancer Res* 13:4623-7s). Aflibercept is the preferred non-antibody VEGF antagonist for use with the invention. Aflibercept is a recombinant human soluble VEGF receptor fusion protein consisting of portions of human VEGF receptors 1 and 2 extracellular domains fused to the Fc portion of human IgG1. It is a dimeric glycoprotein with a protein molecular weight of 97 kilodaltons (kDa) and contains glycosylation, constituting an additional 15% of the total molecular mass, resulting in a total molecular weight of 115 kDa. It is conveniently produced as a glycoprotein by expression in recombinant CHO K1 cells. Each monomer can have the following amino acid sequence (SEQ ID NO: 1):

```
SDTGRPFVEMYSEIPEIIHMTEGRELVIPCRVTSPNITVTLKKFPLDTLIPDGKRIIWDSRKGFIISNATY

KEIGLLTCEATVNGHLYKTNYLTHRQTNTIIDVVLSPSHGIELSVGEKLVLNCTARTELNVGIDFNWEYPS

SKHQHKKLVNRDLKTQSGSEMKKFLSTLTIDGVTRSDQGLYTCAASSGLMTKKNSTFVRVHEKDKTHTCPP

CPAPELLGGPSVFLFPPKPKDTLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGNVFSCSVMHEALHNHYTQKSL

SLSPG
``` and disulfide bridges can be formed between residues 30-79, 124-185, 246-306 and 352-410 within each monomer, and between residues 211-211 and 214-214 between the monomers.

Another non-antibody VEGF antagonist immunoadhesin currently in pre-clinical development is a recombinant human soluble VEGF receptor fusion protein similar to VEGF-trap containing extracellular ligand-binding domains 3 and 4 from VEGFR2/KDR, and domain 2 from VEGFR1/Flt-1; these domains are fused to a human IgG Fc protein fragment (Li et al., 2011 *Molecular Vision* 17:797-803). This antagonist binds to isoforms VEGF-A, VEGF-B and VEGF-C. The molecule is prepared using two different production processes resulting in different glycosylation patterns on the final proteins. The two glycoforms are referred to as KH902 (conbercept) and KH906. The fusion protein can have the following amino acid sequence (SEQ ID NO:2):

be produced by the addition or deletion of amino acids. Ordinarily, these amino acid sequence variants will have an amino acid sequence having at least 60% amino acid sequence identity with the amino acid sequences of SEQ ID NO: 1, SEQ ID NO: 2 or SEQ ID NO: 3, preferably at least 80%, more preferably at least 85%, more preferably at least 90%, and most preferably at least 95%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to this sequence is defined herein as the percentage of amino acid residues in the candidate sequence that are identical with SEQ ID NO: 1, SEQ ID NO: 2 or SEQ ID NO: 3, after aligning the sequences and introducing gaps, if necessary, to achieve the maximum percent sequence identity, and not considering any conservative substitutions as part of the sequence identity.

```
MVSYWDTGVLLCALLSCLLLTGSSSGGRPFVEMYSEIPEIIHMTEGRELVIPCRVTSPNITVTLKKFPLDT

LIPDGKRIIWDSRKGFIISNATYKEIGLLTCEATVNGHLYKTNYLTHRQTNTIIDVVLSPSHGIELSVGEK

LVLNCTARTELNVGIDFNWEYPSSKHQHKKLVNRDLKTQSGSEMKKFLSTLTIDGVTRSDQGLYTCAASSG

LMTKKNSTFVRVHEKPFVAFGSGMESLVEATVGERVRLPAKYLGYPPPEIKWYKNGIPLESNHTIKAGHVL

TIMEVSERDTGNYTVILTNPISKEKQSHVVSLVVYVPPGPGDKTHTCPLCPAPELLGGPSVFLFPPKPKDT

LMISRTPEVTCVVVDVSHEDPEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGFYPSDIAVEWESNGQPENNYK

ATPPVLDSDGSFFLYSKLTVDKSRWQQGNVFSCSVMHEALHNHYTQKSLSLSPGK
``` and, like VEGF-trap, can be present as a dimer. This fusion protein and related molecules are further characterized in EP1767546.

Other non-antibody VEGF antagonists include antibody mimetics (e.g. Affibody® molecules, affilins, affitins, anticalins, avimers, Kunitz domain peptides, and monobodies) with VEGF antagonist activity. This includes recombinant binding proteins comprising an ankyrin repeat domain that binds VEGF-A and prevents it from binding to VEGFR-2. One example for such a molecule is DARPin® MP0112. The ankyrin binding domain may have the following amino acid sequence (SEQ ID NO: 3):

Sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM 250 [a standard scoring matrix; see Dayhoff et al., in Atlas of Protein Sequence and Structure, vol. 5, supp. 3 (1978)] can be used in conjunction with the computer program. For example, the

```
GSDLGKKLLEAARAGQDDEVRILMANGADVNTADSTGWTPLHLAVPWGHLEIVEVLLKYGADVNAKDFQGW

TPLHLAAAIGHQEIVEVLLKNGADVNAQDKFGKTAFDISIDNGNEDLAEILQKAA
```

Recombinant binding proteins comprising an ankyrin repeat domain that binds VEGF-A and prevents it from binding to VEGFR-2 are described in more detail in WO2010/060748 and WO2011/135067.

Further specific antibody mimetics with VEGF antagonist activity are the 40 kD pegylated anticalin PRS-050 and the monobody angiocept (CT-322).

The afore-mentioned non-antibody VEGF antagonist may be modified to further improve their pharmacokinetic properties or bioavailability. For example, a non-antibody VEGF antagonist may be chemically modified (e.g., pegylated) to extend its in vivo half-life. Alternatively or in addition, it may be modified by glycosylation or the addition of further glycosylation sites not present in the protein sequence of the natural protein from which the VEGF antagonist was derived.

Variants of the above-specified VEGF antagonists that have improved characteristics for the desired application may percent identity can then be calculated as: the total number of identical matches multiplied by 100 and then divided by the sum of the length of the longer sequence within the matched span and the number of gaps introduced into the longer sequences in order to align the two sequences.

Preferably, the non-antibody VEGF antagonist of the invention binds to VEGF via one or more protein domain(s) that are not derived from the antigen-binding domain of an antibody. The non-antibody VEGF antagonist of the invention are preferably proteinaceous, but may include modifications that are non-proteinaceous (e.g., pegylation, glycosylation).

Therapy

The syringe of the invention may be used to treat an ocular disease, including but not limited to choroidal neovascularisation, age-related macular degeneration (both wet and dry forms), macular edema secondary to retinal vein occlusion (RVO) including both branch RVO (bRVO) and central RVO (cRVO), choroidal neovascularisation secondary to pathologic myopia (PM), diabetic macular edema (DME), diabetic retinopathy, and proliferative retinopathy.

Thus the invention provides a method of treating a patient suffering from of an ocular disease selected from choroidal neovascularisation, wet age-related macular degeneration, macular edema secondary to retinal vein occlusion (RVO) including both branch RVO (bRVO) and central RVO (cRVO), choroidal neovascularisation secondary to pathologic myopia (PM), diabetic macular edema (DME), diabetic retinopathy, and proliferative retinopathy, comprising the step of administering an ophthalmic solution to the patient using a pre-filled syringe of the invention. This method preferably further comprises an initial priming step in which the physician depresses the plunger of the pre-filled syringe to align the pre-determined part of the stopper with the priming mark.

In one embodiment, the invention provides a method of treating an ocular disease selected from choroidal neovascularisation, wet age-related macular degeneration, macular edema secondary to retinal vein occlusion (RVO) including both branch RVO (bRVO) and central RVO (cRVO), choroidal neovascularisation secondary to pathologic myopia (PM), diabetic macular edema (DME), diabetic retinopathy, and proliferative retinopathy, comprising administering a non-antibody VEGF antagonist with a pre-filled syringe of the invention, wherein the patient has previously received treatment with an antibody VEGF antagonist.

Kits

Also provided are kits comprising the pre-filled syringes of the invention. In one embodiment, such a kit comprises a pre-filled syringe of the invention in a blister pack. The blister pack may itself be sterile on the inside. In one embodiment, syringes according to the invention may be placed inside such blister packs prior to undergoing sterilisation, for example terminal sterilisation.

Such a kit may further comprise a needle for administration of the VEGF antagonist. If the VEGF antagonist is to be administered intravitreally, it is typical to use a 30-gauge×½ inch needle, though 31-gauge and 32-gauge needles may be used. For intravitreal administration, 33-gauge or 34-gauge needles could alternatively be used. Such kits may further comprise instructions for use. In one embodiment, the invention provides a carton containing a pre-filled syringe according to the invention contained within a blister pack, a needle and optionally instructions for administration.

Sterilisation

As noted above, a terminal sterilisation process may be used to sterilise the syringe and such a process may use a known process such as an ethylene oxide (EtO) or a hydrogen peroxide ($H_2O_2$) sterilisation process. Needles to be used with the syringe may be sterilised by the same method, as may kits according to the invention.

The package is exposed to the sterilising gas until the outside of the syringe is sterile. Following such a process, the outer surface of the syringe may remain sterile (whilst in its blister pack) for up to 6 months, 9 months, 12 months, 15 months, 18 months, 24 months or longer. Thus, in one embodiment, a syringe according to the invention (whilst in its blister pack) may have a shelf life of up to 6 months, 9 months, 12 months, 15 months, 18 months, 24 months or longer. In one embodiment, less than one syringe in a million has detectable microbial presence on the outside of the syringe after 18 months of storage. In one embodiment, the pre-filled syringe has been sterilised using EtO with a Sterility Assurance Level of at least $10^{-6}$. In one embodiment, the pre-filled syringe has been sterilised using hydrogen peroxide with a Sterility Assurance Level of at least $10^{-6}$. Of course, it is a requirement that significant amounts of the sterilising gas should not enter the variable volume chamber of the syringe. The term "significant amounts" as used herein refers to an amount of gas that would cause unacceptable modification of the ophthalmic solution within the variable volume chamber. In one embodiment, the sterilisation process causes ≤10% (preferably ≤5%, ≤3%, ≤1%) alkylation of the VEGF antagonist. In one embodiment, the pre-filled syringe has been sterilised using EtO, but the outer surface of the syringe has ≤1 ppm, preferably ≤0.2 ppm EtO residue. In one embodiment, the pre-filled syringe has been sterilised using hydrogen peroxide, but the outer surface of the syringe has ≤1 ppm, preferably ≤0.2 ppm hydrogen peroxide residue. In another embodiment, the pre-filled syringe has been sterilised using EtO, and the total EtO residue found on the outside of the syringe and inside of the blister pack is ≤0.1 mg. In another embodiment, the pre-filled syringe has been sterilised using hydrogen peroxide, and the total hydrogen peroxide residue found on the outside of the syringe and inside of the blister pack is ≤0.1 mg.

General

The term "comprising" means "including" as well as "consisting" e.g. a composition "comprising" X may consist exclusively of X or may include something additional e.g. X+Y.

The term "about" in relation to a numerical value x means, for example, x±10%.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of *Current Protocols in Molecular Biology* (F. M. Ausubel et al., eds., 1987) Supplement 30. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) *Adv. Appl. Math.* 2: 482-489

MODES FOR CARRYING OUT THE INVENTION

The invention will now be further described, by way of example only, with reference to the drawings.

Figure 1:
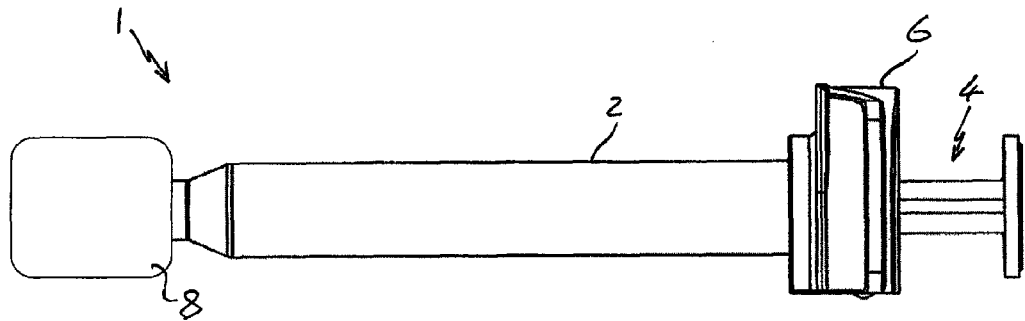
FIG. 1 shows a side view of a syringe

FIG. 1 shows a view from a side of a syringe 1 comprising a body 2, plunger 4, backstop 6 and a sealing device 8.

Figure 2:
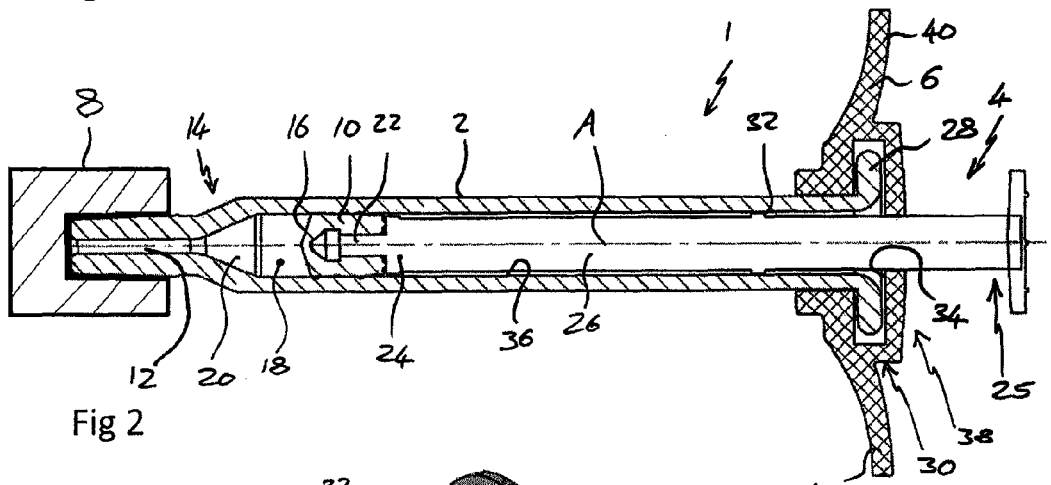
FIG. 2 shows a cross section of a top down view of a syringe

FIG. 2 shows a cross section through the syringe 1 of FIG. 1 from above. The syringe 1 is suitable for use in an ophthalmic injection. The syringe 1 comprises a body 2, a stopper 10 and a plunger 4. The syringe 1 extends along a first axis A. The body 2 comprises an outlet 12 at an outlet end 14 and the stopper 10 is arranged within the body 2 such that a front surface 16 of the stopper 10 and the body 2 define a variable volume chamber 18. The variable volume chamber 18 contains an injectable medicament 20 comprising an ophthalmic solution comprising a VEGF antagonist such as ranibizumab. The injectable fluid 20 can be expelled though the outlet 12 by movement of the stopper 10 towards the outlet end 14 thereby reducing the volume of the variable volume chamber 18. The plunger 4 comprises a plunger contact surface 22 at a first end 24 and a rod 26 extending between the plunger contact surface 22 and a rear portion 25. The plunger contact surface 22 is arranged to contact the stopper 10, such that the plunger 4 can be used to move the stopper 10 towards the outlet end 14 of the body 2. Such movement reduces the volume of the variable volume chamber 18 and causes fluid therein to be expelled though the outlet.

The backstop 6 is attached to the body 2 by coupling to a terminal flange 28 of the body 2. The backstop 6 includes sandwich portion 30 which is adapted to substantially sandwich at least some of the terminal flange 28 of the body 2. The backstop 6 is adapted to be coupled to the body 2 from the side by leaving one side of the backstop 6 open so that the backstop 6 can be fitted to the syringe 2.

The body 2 defines a substantially cylindrical bore 36 which has a bore radius. The rod 26 comprises a rod shoulder 32 directed away from the outlet end 14. The rod shoulder 32 extends from to a rod shoulder radius from the first axis A which is such that it is slightly less than the bore radius so that the shoulder fits within the bore 36. The backstop 6 includes a backstop shoulder 34 directed towards the outlet end 14. The shoulders 32, 34 are configured to cooperate to substantially prevent movement of the rod 26 away from the outlet end 14 when the backstop shoulder 34 and rod shoulder 32 are in contact. The backstop shoulder 34 extends from outside the bore radius to a radius less than the rod shoulder radius so that the rod shoulder 32 cannot pass the backstop shoulder 34 by moving along the first axis A. In this case the rod shoulder 32 is substantially disc, or ring, shaped and the backstop shoulder 34 includes an arc around a rear end 38 of the body 2.

The backstop 6 also includes two finger projections 40 which extend in opposite directions away from the body 2 substantially perpendicular to the first axis A to facilitate manual handling of the syringe 1 during use.

In this example the syringe comprises a 0.5 ml body 2 filled with between about 0.1 and 0.3 ml of an injectable medicament 20 comprising a 10 mg/ml injectable solution comprising ranibizumab. The syringe body 2 has an internal diameter of about between about 4.5 mm and 4.8 mm, a length of between about 45 mm and 50 mm.

The plunger 4 and stopper 10 will be described in more detail with reference to later figures.

Figure 3:
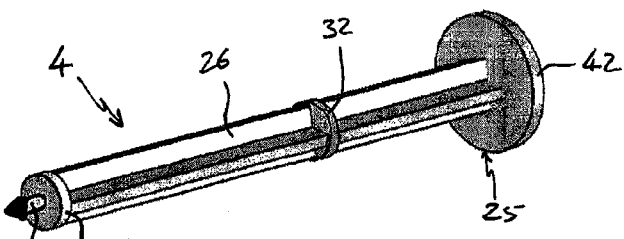
FIG. 3 shows a view of a plunger

FIG. 3 shows a perspective view of the plunger 4 of FIG. 1 showing the plunger contact surface 22 at the first end 24 of the plunger 4. The rod 26 extends from the first end 24 to the rear portion 25. The rear portion 25 includes a disc shaped flange 42 to facilitate user handling of the device. The flange 42 provides a larger surface area for contact by the user than a bare end of the rod 26.

Figure 4:
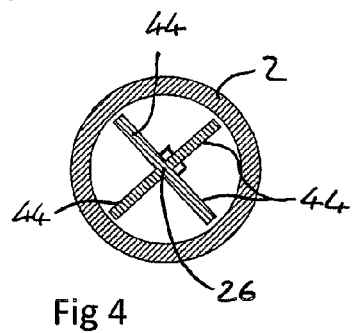
FIG. 4 shows a cross section though a plunger

FIG. 4 shows a cross section though a syringe body 2 and rod 26. The rod 26 includes four longitudinal ribs 44 and the angle between the ribs is 90°.

Figure 5:
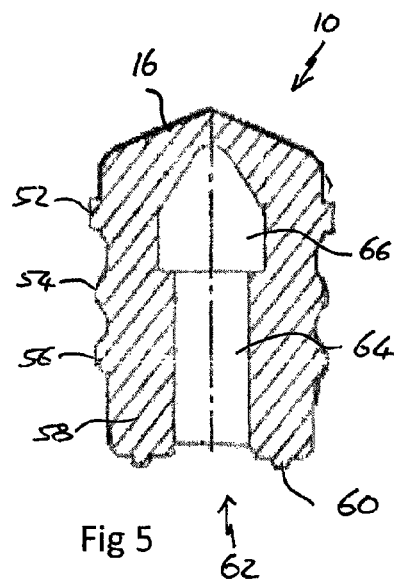
FIG. 5 shows a stopper

FIG. 5 shows a detailed view of a stopper 10 showing a conical shaped front surface 16 and three circumferential ribs 52, 54, 56 around a substantially cylindrical body 58. The axial gap between the first rib 52 and the last rib 56 is about 3 mm. The rear surface 60 of the stopper 10 includes a substantially central recess 62. The central recess 62 includes an initial bore 64 having a first diameter. The initial bore 64 leading from the rear surface 60 into the stopper 10 to an inner recess 66 having a second diameter, the second diameter being larger than the first diameter.

Stopper Movement Forces 0.5 ml syringes siliconised with <100 µg silicone oil, filled with Lucentis, comprising one of two different stopper designs were tested for maximal and average break out and slide force. Prior to testing, 30 G×0.5" needles were attached to the syringes. The testing was carried out at a stopper speed of 190 mm/min over a travel length of 10.9 mm. Stopper design 2 had a 45% increase in the distance between the front circumferential rib and rear circumferential rib.

|  |  | Stopper design 1 | | | Stopper design 2 | |
|---|---|---|---|---|---|---|
|  |  | Batch A | Batch B | Batch C | Batch D | Batch E |
| Break loose force of syringes | Average of 10 syringes | 2.2N | 2.3N | 1.9N | 2.1N | 2.5N |
|  | Max individual value | 2.5N | 2.5N | 2.3N | 2.6N | 2.7N |
| Sliding force | Average of 10 syringes | 3.1N | 3.2N | 3.1N | 4.1N | 4.6N |
|  | Max individual value | 3.5N | 3.5N | 3.6N | 4.7N | 4.8N |

For both stopper designs, average and maximum break out force remained below 3N. For both stopper designs, average and maximum sliding force remained below 5N.

It will be understood that the invention has been described by way of example only and modifications may be made whilst remaining within the scope and spirit of the invention.

The invention claimed is:

1. A pre-filled, terminally sterilized syringe for intravitreal injection, the syringe comprising a glass body forming a barrel, a stopper and a plunger and containing an ophthalmic solution which comprises a VEGF-antagonist, wherein:
   (a) the syringe has a nominal maximum fill volume of between about 0.5 ml and about 1 ml,
   (b) the syringe barrel comprises from about 1 μg to 100 ug silicone oil,
   (c) the VEGF antagonist solution comprises no more than 2 particles >50 μm in diameter per ml and wherein the syringe has a stopper break loose force of less than about 11N.

2. A pre-filled syringe according to claim 1, wherein the syringe barrel has an internal coating of silicone oil that has an average thickness of about 450 nm or less.

3. A pre-filled syringe according to claim 1, wherein the syringe barrel has an internal coating of from about 3 μg to about 100 ug silicone oil.

4. A pre-filled syringe according to claim 1, wherein the silicone oil is DC365 emulsion.

5. A pre-filled syringe according to claim 1, wherein the VEGF antagonist solution further comprises one or more of (i) no more than 5 particles ≥25 μm in diameter per ml, and (ii) no more than 50 particles ≥10 μm in diameter per ml.

6. A pre-filled syringe according to claim 1, wherein the VEGF antagonist solution meets USP789.

7. A pre-filled syringe according to claim 1, wherein the VEGF antagonist is an anti-VEGF antibody.

8. A pre-filled syringe according to claim 7, wherein the anti-VEGF antibody is ranibizumab.

9. A pre-filled syringe according to claim 8, wherein the ranibizumab is at a concentration of 10 mg/ml.

10. A pre-filled syringe according to claim 8, wherein the silicone oil has a viscosity of about 350 cP, and the VEGF antagonist solution further comprises one or more of (i) no more than 5 particles ≥25 μm in diameter per ml, and (ii) no more than 50 particles ≥10 μm in diameter per ml.

11. A pre-filled syringe according to claim 1 wherein the VEGF antagonist is a non-antibody VEGF antagonist.

12. A pre-filled syringe according to claim 11, wherein the non-antibody VEGF antagonist is aflibercept or conbercept.

13. A pre-filled syringe according to claim 12, wherein the non-antibody VEGF antagonist is aflibercept at a concentration of 40 mg/ml.

14. A pre-filled syringe according to claim 1, wherein the syringe has a stopper break loose force of less than about 5N, and wherein the syringe has a stopper slide force of less than about 5N.

15. A pre-filled syringe according to claim 14, wherein the stopper break loose force or stopper slide force is measured using a filled syringe, at a stopper travelling speed of 190 mm/min, with a 30 G×0.5 inch needle attached to the syringe.

16. A pre-filled syringe according to claim 1, wherein the syringe has a stopper slide force of less than about 11N.

17. A blister pack comprising a pre-filled syringe according to claim 1, wherein the syringe has been sterilised using $H_2O_2$ or EtO.

18. A blister pack comprising a pre-filled syringe according to claim 17, wherein the outer surface of the syringe has ≤1 ppm EtO or $H_2O_2$ residue.

19. A blister pack comprising a pre-filled syringe according to claim 17, wherein the syringe has been sterilised using EtO or $H_2O_2$ and the total EtO or $H_2O_2$ residue found on the outside of the syringe and inside of the blister pack is ≤0.1 mg.

20. A blister pack comprising a pre-filled syringe according to claim 18, wherein ≤5% of the VEGF antagonist is alkylated.

21. A blister pack comprising a pre-filled syringe according to claim 17, wherein the syringe has been sterilised using EtO or $H_2O_2$ with a Sterility Assurance Level of at least $10^{-6}$.

22. A pre-filled syringe according to claim 1, wherein the syringe barrel has an internal coating of from about 1-50 μg silicone oil.

23. A pre-filled syringe according to claim 1, wherein the silicone oil has a viscosity of about 350 cP.

24. A method of treating a patient suffering from of an ocular disease selected from choroidal neovascularisation, wet age-related macular degeneration, macular edema secondary to retinal vein occlusion (RVO) including both branch RVO (bRVO) and central RVO (cRVO), choroidal neovascularisation secondary to pathologic myopia (PM), diabetic macular edema (DME), diabetic retinopathy, and proliferative retinopathy, comprising the step of administering an ophthalmic solution to the patient using a pre-filled syringe according to claim 1.

25. The method of claim 24, further comprising an initial priming step in which the physician depresses the plunger of the pre-filled syringe to align the pre-determined part of the stopper with the priming mark.

26. A method according to claim 24, wherein the VEGF antagonist administered is a non-antibody VEGF antagonist and wherein the patient has previously received treatment with an antibody VEGF antagonist.

* * * * *

SEQUENCE LISTING

```
<160> NUMBER OF SEQ ID NOS: 3

<210> SEQ ID NO 1
<211> LENGTH: 431
<212> TYPE: PRT
<213> ORGANISM: Artificial Sequence
<220> FEATURE:
<223> OTHER INFORMATION: aflibercept

<400> SEQUENCE: 1

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30
```

Thr Ser Pro Asn Ile Thr Val Thr Leu Lys Lys Phe Pro Leu Asp Thr
         35                  40                  45

Leu Ile Pro Asp Gly Lys Arg Ile Ile Trp Asp Ser Arg Lys Gly Phe
 50                  55                  60

Ile Ile Ser Asn Ala Thr Tyr Lys Glu Ile Gly Leu Leu Thr Cys Glu
 65                  70                  75                  80

Ala Thr Val Asn Gly His Leu Tyr Lys Thr Asn Tyr Leu Thr His Arg
                 85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly
            420                 425                 430

<210> SEQ ID NO 2
<211> LENGTH: 552
<212> TYPE: PRT

<213> ORGANISM: Artificial Sequence
<220> FEATURE:
<223> OTHER INFORMATION: conbercept

<400> SEQUENCE: 2

```
Met Val Ser Tyr Trp Asp Thr Gly Val Leu Leu Cys Ala Leu Leu Ser
1               5                   10                  15

Cys Leu Leu Leu Thr Gly Ser Ser Gly Gly Arg Pro Phe Val Glu
            20                  25                  30

Met Tyr Ser Glu Ile Pro Glu Ile Ile His Met Thr Glu Gly Arg Glu
        35                  40                  45

Leu Val Ile Pro Cys Arg Val Thr Ser Pro Asn Ile Thr Val Thr Leu
    50                  55                  60

Lys Lys Phe Pro Leu Asp Thr Leu Ile Pro Asp Gly Lys Arg Ile Ile
65                  70                  75                  80

Trp Asp Ser Arg Lys Gly Phe Ile Ile Ser Asn Ala Thr Tyr Lys Glu
                85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Val Val
        115                 120                 125

Leu Ser Pro Ser His Gly Ile Glu Leu Ser Val Gly Glu Lys Leu Val
    130                 135                 140

Leu Asn Cys Thr Ala Arg Thr Glu Leu Asn Val Gly Ile Asp Phe Asn
145                 150                 155                 160

Trp Glu Tyr Pro Ser Ser Lys His Gln His Lys Lys Leu Val Asn Arg
                165                 170                 175

Asp Leu Lys Thr Gln Ser Gly Ser Glu Met Lys Lys Phe Leu Ser Thr
            180                 185                 190

Leu Thr Ile Asp Gly Val Thr Arg Ser Asp Gln Gly Leu Tyr Thr Cys
        195                 200                 205

Ala Ala Ser Ser Gly Leu Met Thr Lys Lys Asn Ser Thr Phe Val Arg
    210                 215                 220

Val His Glu Lys Pro Phe Val Ala Phe Gly Ser Gly Met Glu Ser Leu
225                 230                 235                 240

Val Glu Ala Thr Val Gly Glu Arg Val Arg Leu Pro Ala Lys Tyr Leu
                245                 250                 255

Gly Tyr Pro Pro Pro Glu Ile Lys Trp Tyr Lys Asn Gly Ile Pro Leu
            260                 265                 270

Glu Ser Asn His Thr Ile Lys Ala Gly His Val Leu Thr Ile Met Glu
        275                 280                 285

Val Ser Glu Arg Asp Thr Gly Asn Tyr Thr Val Ile Leu Thr Asn Pro
    290                 295                 300

Ile Ser Lys Glu Lys Gln Ser His Val Val Ser Leu Val Val Tyr Val
305                 310                 315                 320

Pro Pro Gly Pro Gly Asp Lys Thr His Thr Cys Pro Leu Cys Pro Ala
                325                 330                 335

Pro Glu Leu Leu Gly Gly Pro Ser Val Phe Leu Phe Pro Pro Lys Pro
            340                 345                 350

Lys Asp Thr Leu Met Ile Ser Arg Thr Pro Glu Val Thr Cys Val Val
        355                 360                 365

Val Asp Val Ser His Glu Asp Pro Glu Val Lys Phe Asn Trp Tyr Val
    370                 375                 380

Asp Gly Val Glu Val His Asn Ala Lys Thr Lys Pro Arg Glu Glu Gln
```

```
                385                 390                 395                 400
Tyr Asn Ser Thr Tyr Arg Val Val Ser Val Leu Thr Val Leu His Gln
                    405                 410                 415

Asp Trp Leu Asn Gly Lys Glu Tyr Lys Cys Lys Val Ser Asn Lys Ala
                420                 425                 430

Leu Pro Ala Pro Ile Glu Lys Thr Ile Ser Lys Ala Lys Gly Gln Pro
                435                 440                 445

Arg Glu Pro Gln Val Tyr Thr Leu Pro Pro Ser Arg Asp Glu Leu Thr
                450                 455                 460

Lys Asn Gln Val Ser Leu Thr Cys Leu Val Lys Gly Phe Tyr Pro Ser
465                 470                 475                 480

Asp Ile Ala Val Glu Trp Glu Ser Asn Gly Gln Pro Glu Asn Asn Tyr
                485                 490                 495

Lys Ala Thr Pro Pro Val Leu Asp Ser Asp Gly Ser Phe Phe Leu Tyr
                500                 505                 510

Ser Lys Leu Thr Val Asp Lys Ser Arg Trp Gln Gln Gly Asn Val Phe
                515                 520                 525

Ser Cys Ser Val Met His Glu Ala Leu His Asn His Tyr Thr Gln Lys
                530                 535                 540

Ser Leu Ser Leu Ser Pro Gly Lys
545                 550

<210> SEQ ID NO 3
<211> LENGTH: 126
<212> TYPE: PRT
<213> ORGANISM: Artificial Sequence
<220> FEATURE:
<223> OTHER INFORMATION: DARPin MP0112

<400> SEQUENCE: 3

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Thr
                20                  25                  30

Ala Asp Ser Thr Gly Trp Thr Pro Leu His Leu Ala Val Pro Trp Gly
                35                  40                  45

His Leu Glu Ile Val Glu Val Leu Leu Lys Tyr Gly Ala Asp Val Asn
                50                  55                  60

Ala Lys Asp Phe Gln Gly Trp Thr Pro Leu His Leu Ala Ala Ala Ile
65                  70                  75                  80

Gly His Gln Glu Ile Val Glu Val Leu Leu Lys Asn Gly Ala Asp Val
                85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Ala Ala
                115                 120                 125
```